United States Patent [19]
Coussens et al.

[11] Patent Number: 5,827,738
[45] Date of Patent: Oct. 27, 1998

[54] SUSTAINABLE CHICK CELL LINE INFECTED WITH MAREK'S DISEASE VIRUS

[75] Inventors: Paul M. Coussens, DeWitt; Amin Abujoub, East Lansing, both of Mich.

[73] Assignee: Board of Trustees operating Michigan State University, East Lansing, Mich.

[21] Appl. No.: 549,045

[22] Filed: Oct. 27, 1995

[51] Int. Cl.$^6$ .............................. C12N 5/10; C12N 5/00
[52] U.S. Cl. ............................................ 435/349; 435/325
[58] Field of Search ...................................... 435/240, 325, 435/349, 172.3; 424/93.21; 514/44

[56] References Cited

PUBLICATIONS

Ikuta, Kazuyoshi, et al. 1987. International Journal of Cancer, vol. 39, pp. 514–520.
Calnek, B.W., and R. L. Witter, in "Diseases of Poultry: Marek's Disease" (B.W.Calnek,et al.,Eds.), pp. 342–385. Iowa State University Press, Ames, Iowa (1991).
Witter, R. L., et al., J. Natl. Cancer Inst. 49:1121–1130 (1972).
Calnek, B. W., et al., Avian Dis. 14:219–233 (1970).
Shek, W. R., et al., J. Natl. Cancer Inst. 70:485–491 (1983).
Akiyama, Y., et al., Continuous Cell Culture from lymphoma of Marek's disease, Biken J. 16:177–179 (1973).
Akiyama, Y., et al., Two cell lines from lymphomas of Marek's disease. Biken J. 17:105–116 (1974).
Powell, P.C., et al., Nature 251:79–80 (1974).
Calnek, B.W., et al., Int. J. Cancer 21:100–107 (1978).
Payne, L. N., et al., Int. J. Cancer 28:757–766 (1981).
Nazerian K., and R.L. Witter, J. Natl. Cancer Inst. 54:435–458 (1975).
Delecluse, H.–J., et al., J. Virol. 67:82–92 (1993).
Maray, T., et al., Virus Genes 2:49–68 (1988).
Sugaya, K., et al., J. Virol. 64:5773–5782 (1990).
Schat, K. A., et al., Int. J. Cancer 44:101–109 (1989).
Nazerian, K., et al., Avian Diseases 21:69–76 (1977).
Witter, R.L., Avian Path. 11:49–62 (1982).
Witter, R. L. and L. F. Lee, Avian Path. 13:75–92 (1984).
Witter, R. L., Principles of Vaccination.In "Marek's Disease:Scientific Basis and Methods of Control" (Payne,L.N.,ed.) pp. 203–250 (1985).
Nazerian, K., an updated list of avian cell lines and transplantable tumors.Avian Path.12:527–544 (1987).
Churchill, A.E.,Production of Vaccines. In Marek's Disease:Scientific Basis and Methods of Control pp. 251–265. Marinus Nijhoff PUb.Co.Boston,(1985).
Glaubiger, C., et al., J. Virol. 45:1228–1234 (1983).
Coussens, P.M., and L.F. Velicer, J. Virol. 62:2373–2379 (1988).
Ogura, H., et al., Acta Med. Okayama 41:141–143 (1987).
Sambrook,J., et al., Molecular cloning a laboratory manual. 2nd ed. Cold Spring Harbor Lab. Cold Spring Harbor, NY (1989).
Cui, Z., et al., J. Virol. 65:6509–6515 (1991).
Hong, Y., and P. M. Coussens,, J. Virol. 68:3593–3603 (1994).

*Primary Examiner*—David Guzo
*Assistant Examiner*—Matthew Latimer
*Attorney, Agent, or Firm*—Ian C. McLeod

[57] ABSTRACT

A sustainable cell line of a Marek's disease herpesvirus (MDV) infected chicken cell line derived from chick embryo cells which are chicken helper factor (Chf) negative and which have been treated with N-methyl-N-nitro-N-nitrosoguansidine (MNNG) and then converted with the MDV which is able to infect avians in vivo. The cell line is useful for vaccine production and for determining the characteristics of the MDV under various conditions.

17 Claims, 5 Drawing Sheets

SEQUENCE LISTING ( 1 ) GENERAL INFORMATION:

( i i i ) NUMBER OF SEQUENCES: 14

( 2 ) INFORMATION FOR SEQ ID NO:1:

( i ) SEQUENCE CHARACTERISTICS:
        ( A ) LENGTH: 21 Base Pairs
        ( B ) TYPE: Nucleic Acid
        ( C ) STRANDEDNESS: Single
        ( D ) TOPOLOGY: Linear     ( i i ) MOLECULE TYPE:
        ( A ) DESCRIPTION: Synthetic DNA     ( i i i ) HYPOTHETICAL: No     ( i v ) ANTI-SENSE: No     ( v i ) ORIGINAL SOURCE:
        ( A ) ORGANISM: Marek's Disease Virus     ( v i i ) IMMEDIATE SOURCE:

(A) LIBRARY:

(xi) SEQUENCE DESCRIPTION: SEQ ID NO: 1:

GTAGTGAAAT CTATACCTGG G                                                                                      21

(2) INFORMATION FOR SEQ ID NO:2:

(i) SEQUENCE CHARACTERISTICS:
        (A) LENGTH: 33 Base Pairs
        (B) TYPE: Nucleic Acid
        (C) STRANDEDNESS: Single
        (D) TOPOLOGY: Linear     (ii) MOLECULE TYPE:
        (A) DESCRIPTION: Synthetic DNA     (iii) HYPOTHETICAL: No     (iv) ANTI-SENSE: No     (vi) ORIGINAL SOURCE:
        (A) ORGANISM: Marek's Disease Virus     (vii) IMMEDIATE SOURCE:
        (A) LIBRARY:

(xi) SEQUENCE DESCRIPTION: SEQ ID NO: 2:

GTGTCTAGAG AGGGAAGATA TGTAGAGGGT TAC                                                          33

(2) INFORMATION FOR SEQ ID NO:3:

(i) SEQUENCE CHARACTERISTICS:
        (A) LENGTH: 21 Base Pairs
        (B) TYPE: Nucleic Acid
        (C) STRANDEDNESS: Single
        (D) TOPOLOGY: Linear     (ii) MOLECULE TYPE:
        (A) DESCRIPTION: Synthetic DNA     (iii) HYPOTHETICAL: No     (iv) ANTI-SENSE: No     (vi) ORIGINAL SOURCE:
        (A) ORGANISM: Marek's Disease Virus     (vii) IMMEDIATE SOURCE:
        (A) LIBRARY:

(xi) SEQUENCE DESCRIPTION: SEQ ID NO: 3:

ATGGAATTCG AAGCAGAACA C                                                                                      21

(2) INFORMATION FOR SEQ ID NO:4:

(i) SEQUENCE CHARACTERISTICS:
        (A) LENGTH: 22 Base Pairs
        (B) TYPE: Nucleic Acid
        (C) STRANDEDNESS: Single
        (D) TOPOLOGY: Linear     (ii) MOLECULE TYPE:
        (A) DESCRIPTION: Synthetic DNA     (iii) HYPOTHETICAL: No     (iv) ANTI-SENSE: No     (vi) ORIGINAL SOURCE:
        (A) ORGANISM: Marek's Disease Virus     (vii) IMMEDIATE SOURCE:
        (A) LIBRARY:

( x i ) SEQUENCE DESCRIPTION: SEQ ID NO: 4:

CTCCAGATTC CACCTCCCCA GA 22

( 2 ) INFORMATION FOR SEQ ID NO:5:

( i ) SEQUENCE CHARACTERISTICS:
        ( A ) LENGTH: 16 Base Pairs
        ( B ) TYPE: Nucleic Acid
        ( C ) STRANDEDNESS: Single
        ( D ) TOPOLOGY: Linear     ( i i ) MOLECULE TYPE:
        ( A ) DESCRIPTION: Synthetic DNA     ( i i i ) HYPOTHETICAL: No     ( i v ) ANTI-SENSE: No     ( v i ) ORIGINAL SOURCE:
        ( A ) ORGANISM: Marek's Disease Virus     ( v i i ) IMMEDIATE SOURCE:
        ( A ) LIBRARY:

( x i ) SEQUENCE DESCRIPTION: SEQ ID NO: 5:

TGCTAATTGT GGCTCC 16

( 2 ) INFORMATION FOR SEQ ID NO:6:

( i ) SEQUENCE CHARACTERISTICS:
        ( A ) LENGTH: 17 Base Pairs
        ( B ) TYPE: Nucleic Acid
        ( C ) STRANDEDNESS: Single
        ( D ) TOPOLOGY: Linear     ( i i ) MOLECULE TYPE:
        ( A ) DESCRIPTION: Synthetic DNA     ( i i i ) HYPOTHETICAL: No     ( i v ) ANTI-SENSE: No     ( v i ) ORIGINAL SOURCE:
        ( A ) ORGANISM: Marek's Disease Virus     ( v i i ) IMMEDIATE SOURCE:
        ( A ) LIBRARY:

( x i ) SEQUENCE DESCRIPTION: SEQ ID NO: 6:

GGTGCTTCCA TCTCGGC 17

( 2 ) INFORMATION FOR SEQ ID NO:7:

( i ) SEQUENCE CHARACTERISTICS:
        ( A ) LENGTH: 27 Base Pairs
        ( B ) TYPE: Nucleic Acid
        ( C ) STRANDEDNESS: Single
        ( D ) TOPOLOGY: Linear     ( i i ) MOLECULE TYPE:
        ( A ) DESCRIPTION: Synthetic DNA     ( i i i ) HYPOTHETICAL: No     ( i v ) ANTI-SENSE: No     ( v i ) ORIGINAL SOURCE:
        ( A ) ORGANISM: Marek's Disease Virus     ( v i i ) IMMEDIATE SOURCE:
        ( A ) LIBRARY:

( x i ) SEQUENCE DESCRIPTION: SEQ ID NO: 7:

GATCTAGACG TTTCTGCCTC CGGAGTC 27

( 2 ) INFORMATION FOR SEQ ID NO:8:

( i ) SEQUENCE CHARACTERISTICS:
        ( A ) LENGTH: 30 Base Pairs
        ( B ) TYPE: Nucleic Acid
        ( C ) STRANDEDNESS: Single
        ( D ) TOPOLOGY: Linear     ( i i ) MOLECULE TYPE:
        ( A ) DESCRIPTION: Synthetic DNA     ( i i i ) HYPOTHETICAL: No     ( i v ) ANTI-SENSE: No     ( v i ) ORIGINAL SOURCE:
        ( A ) ORGANISM: Marek's Disease Virus     ( v i i ) IMMEDIATE SOURCE:
        ( A ) LIBRARY:

( x i ) SEQUENCE DESCRIPTION: SEQ ID NO: 8:

GCAAGCTTCA ACATCTTCAA ATAGCCGCAC 30

( 2 ) INFORMATION FOR SEQ ID NO:9:

( i ) SEQUENCE CHARACTERISTICS:
        ( A ) LENGTH: 29 Base Pairs
        ( B ) TYPE: Nucleic Acid
        ( C ) STRANDEDNESS: Single
        ( D ) TOPOLOGY: Linear     ( i i ) MOLECULE TYPE:
        ( A ) DESCRIPTION: Synthetic DNA     ( i i i ) HYPOTHETICAL: No     ( i v ) ANTI-SENSE: No     ( v i ) ORIGINAL SOURCE:
        ( A ) ORGANISM: Marek's Disease Virus     ( v i i ) IMMEDIATE SOURCE:
        ( A ) LIBRARY:

( x i ) SEQUENCE DESCRIPTION: SEQ ID NO: 9:

GTCTAGACGC GATAGCGAGT TGTTGGACC 29

( 2 ) INFORMATION FOR SEQ ID NO:10:

( i ) SEQUENCE CHARACTERISTICS:
        ( A ) LENGTH: 28 Base Pairs
        ( B ) TYPE: Nucleic Acid
        ( C ) STRANDEDNESS: Single
        ( D ) TOPOLOGY: Linear     ( i i ) MOLECULE TYPE:
        ( A ) DESCRIPTION: Synthetic DNA     ( i i i ) HYPOTHETICAL: No     ( i v ) ANTI-SENSE: No     ( v i ) ORIGINAL SOURCE:
        ( A ) ORGANISM: Marek's Disease Virus     ( v i i ) IMMEDIATE SOURCE:
        ( A ) LIBRARY:

( x i ) SEQUENCE DESCRIPTION: SEQ ID NO: 10:

GGAAGCTTTA TTAAGGGAGA TTCTACCC 28

( 2 ) INFORMATION FOR SEQ ID NO:11:

( i ) SEQUENCE CHARACTERISTICS:
        ( A ) LENGTH: 20 Base Pairs
        ( B ) TYPE: Nucleic Acid
        ( C ) STRANDEDNESS: Single
        ( D ) TOPOLOGY: Linear     ( i i ) MOLECULE TYPE:
        ( A ) DESCRIPTION: Synthetic DNA     ( i i i ) HYPOTHETICAL: No     ( i v ) ANTI-SENSE: No     ( v i ) ORIGINAL SOURCE:
        ( A ) ORGANISM: Marek's Disease Virus     ( v i i ) IMMEDIATE SOURCE:
        ( A ) LIBRARY:

( x i ) SEQUENCE DESCRIPTION: SEQ ID NO: 11:

GTGAAAGAGT GAACGGGAAG        20

( 2 ) INFORMATION FOR SEQ ID NO:12:

( i ) SEQUENCE CHARACTERISTICS:
        ( A ) LENGTH: 19 Base Paris
        ( B ) TYPE: Nucleic Acid
        ( C ) STRANDEDNESS: Single
        ( D ) TOPOLOGY: Linear     ( i i ) MOLECULE TYPE:
        ( A ) DESCRIPTION: Synthetic DNA     ( i i i ) HYPOTHETICAL: No     ( i v ) ANTI-SENSE: No     ( v i ) ORIGINAL SOURCE:
        ( A ) ORGANISM: Marek's Disease Virus     ( v i i ) IMMEDIATE SOURCE:
        ( A ) LIBRARY:

( x i ) SEQUENCE DESCRIPTION: SEQ ID NO: 12:

CGTCAAAGCG ATAATAGGC        19

( 2 ) INFORMATION FOR SEQ ID NO:13:

( i ) SEQUENCE CHARACTERISTICS:
        ( A ) LENGTH: 30 Base Pairs
        ( B ) TYPE: Nucleic Acid
        ( C ) STRANDEDNESS: Single
        ( D ) TOPOLOGY: Linear     ( i i ) MOLECULE TYPE:
        ( A ) DESCRIPTION: Synthetic DNA     ( i i i ) HYPOTHETICAL: No     ( i v ) ANTI-SENSE: No     ( v i ) ORIGINAL SOURCE:
        ( A ) ORGANISM: Marek's Disease Virus     ( v i i ) IMMEDIATE SOURCE:
        ( A ) LIBRARY:

( x i ) SEQUENCE DESCRIPTION: SEQ ID NO: 13:

CCGGGGATCC CGAAATGTCG TTAGAACATC        30

( 2 ) INFORMATION FOR SEQ ID NO:14:

```
( i ) SEQUENCE CHARACTERISTICS:
        ( A ) LENGTH: 28 Base Pairs
        ( B ) TYPE: Nucleic Acid
        ( C ) STRANDEDNESS: Single
        ( D ) TOPOLOGY: Linear ( i i ) MOLECULE TYPE:
        ( A ) DESCRIPTION: Synthetic DNA ( i i i ) HYPOTHETICAL: No ( i v ) ANTI-SENSE: No ( v i ) ORIGINAL SOURCE:
        ( A ) ORGANISM: Marek's Disease Virus ( v i i ) IMMEDIATE SOURCE:
        ( A ) LIBRARY:

( x i ) SEQUENCE DESCRIPTION: SEQ ID NO: 14:

CGGGGTCGAC   TAAGGCAAAT   AGGCACGC                                                           2 8
```

SUSTAINABLE CHICK CELL LINE INFECTED WITH MAREK'S DISEASE VIRUS

BACKGROUND OF THE INVENTION

1. Summary of the Invention

The present invention relates to a sustainable chicken cell line infected with Marek's disease virus (MDV). In particular, the present invention relates to a cell line which can be used as a virus vaccine, as a system in which to produce altered MDV strains, and which can be used to determine the affect of various reagents or growth conditions on the cell line over time.

2. Description of Related Art

Marek's disease (MD) is a highly contagious lymphoproliferative disease of chickens, characterized by lymphocytic infiltration in visceral organs, muscles, and peripheral nerves. The etiological agent of MD, an avian herpesvirus called Marek's disease virus (MDV), is highly infectious and cell associated (Calnek, B. W., and R. L. Witter, In "Diseases of Poultry: Marek's Disease" (B. W. Calnek, et al., Eds.), pp. 342–385. Iowa State University press, Ames, Iowa (1991)). MDV replicates in a productive restrictive manner in B-lymphocytes and cells growing in tissue culture. Production of fully enveloped virus is restricted to feather follicle epithelium of infected birds (Witter, R. L., et al., J. Natl. Cancer Inst. 49:1121–1130 (1972); Calnek, B. W., et al., Avian Dis. 14:219–233 (1970)). MDV rapidly establishes a latent infection in T-lymphocytes, ultimately leading to malignant transformation and neoplastic disease (Shek, W. R., et al., J. Natl. Cancer Inst. 70:485–491 (1983)). However, the precise relationship between latency and transformation in MDV infected T-lymphocytes is unknown. Akiyama, Y., et al. (Continuous cell culture from lymphoma of Marek's disease. Biken J. 16:177–179 (1973)) first succeeded in establishing a T-lymphoblastoid cell line from MD-infected chickens. Since then, more than 80 cell lines have been produced from MD lymphomas (Akiyama, Y., et al., Two cell lines from lymphomas of Marek's disease. Biken J. 17:105–116 (1974); Powell, P. C., et al., Nature 251:79–80 (1974); Calnek, B. W., et al., Int. J. Cancer 21:100–107 (1978); Payne, L. N., et al., Int. J. Cancer 28:757–766 (1981); Nazerian K., and R. L. Witter, J. Natl. Cancer Inst. 54:435–458 (1975)). Although suitable for some studies, these cell lines are many passages removed from the original event(s) leading to their transformation.

Evidence suggests that viral genomes in MD-lymphoblastoid cell lines are predominately integrated into cellular chromosomes, but episomal forms also exist (Delecluse, H.-J., et al., J. Virol. 67:82–92 (1993)). Analysis of viral transcription in transformed lymphoblastoid cell lines has revealed variable but limited transcriptional activity confined to approximately 20% of the viral genome (Maray, T., et al., Virus Genes 2:49–68 (1988)). MDV-specific transcripts in transformed lymphoblastoid cells are primarily derived from within long and short region terminal repeats ($TR_L$ and $TR_S$ respectively) and internal repeats ($IR_L$ and $IR_R$ respectively). Little transcriptional activity is detected within either the long unique ($U_L$) or short unique ($U_S$) regions (Sugaya, K., et al., J. Virol. 64:5773–5782 (1990)). MDV can be rescued from some lymphoblastoid cell lines by co-cultivation with primary or secondary chicken and duck embryo fibroblasts (CEF and DEF, respectively), which support the lytic cycle of MDV in vitro (Schat, K. A., et al., Int. J. Cancer 44:101–109 (1989)). In addition, some lymphoblastoid cell lines will induce MD upon injection into susceptible birds (Akiyama, Y., et al., Continuous cell culture from lymphoma of Marek's disease. Biken J. 16:177–179 (1973); Nazerian, K., et al., Avian Diseases 21:69–76 (1977)).

Since development of live virus Marek's disease vaccines in the late 1970's, losses to Marek's disease have been significantly reduced (Calnek and Witter, In "Diseases of Poultry: Marek's Disease" (B. W. Calnek, H. J. Barnes, C. W. Beard, W. M. Reid, and H. W. Yoder, Jr., Eds.), pp. 342–385. Iowa State University press, Ames IA (1991)). The most widely used Marek's disease vaccines are live Turkey herpesvirus (HVT or serotype 3 MDV) or a bivalent mixture of HVT and the apathogenic serotype 2 strain of MDV (MDV-2). The bivalent mixture of HVT and serotype 2 MDV synergistically affords greater protection against Marek's disease, especially in those situations where HVT is not fully effective (Witter, R. L., Protection by attenuated and polyvalent vaccines against highly virulent strain of Marek's disease virus. Avian Path. 11:49–62 (1982); Witter, R. L. and L. F. Lee, Polyvalent Marek's disease vaccines: safety, efficacy and protective synergism in chickens with maternal antibodies. Avian Path. 13:75–92 (1984); Witter, R. L., Principles of Vaccination. In "Marek's Disease: Scientific Basis and Methods of Control" (Payne, L. N., ed.) pp. 203–250. Marinus Nijhoff Pub., Boston, Mass. (1985)). Marek's disease vaccines are the most widely used vaccines in the poultry industry. Current Marek's disease vaccines are either suspensions of infected chicken embryo fibroblasts (CEF) or cell-free virus suspensions made from sonicated CEF infected with vaccine strains of Marek's disease virus (MDV).

Two major difficulties in working with MDV are the strongly cell associated nature of the virus and the lack a sustainable cell culture system amenable to productive (lytic) infections. Primary CEF and DEF are permissive for MDV replication. However, these cultures have a finite life span (approximately 3 weeks), thus necessitating passage of infected primary cells onto an uninfected cell monolayer to propagate MDV and to obtain sufficient quantities of virus with which to work. Such conditions also preclude establishment of one-step growth experiments for effective temporal gene regulation studies. The finite life span of CEF and DEF also make positive selection in mutagenesis studies difficult.

The poultry industry has always recognized the need for continuous avian cell lines that could be used in producing Marek's disease vaccines and simplify development of recombinant MDV vectors for polyvalent vaccines. Although many avian cell lines have been developed (Nazarian, K., An updated list of avian cell lines and transplantable tumors. Avian Path. 12:527–544 (1987)), none of these can substitute for CEF cells in vaccine production. Previous cell lines failed because they were either derived from virally transformed cells or, if derived from chemically transformed cells, the cells produced tumors when inoculated into chickens. Since there are no sustainable cell lines suitable for propagating MDV, the MDV vaccine industry uses primary chicken embryo fibroblasts (CEF) for production of vaccine virus (Churchill, A. E., Production of Vaccines. In "Marek's Disease: Scientific Basis and Methods of Control" (Payne, L. N., ed.), pp. 251–265. Marinus Nijhoff Publishing, Boston, Massachusetts (1985)). Since primary CEFs have a finite life span, they must be prepared every week, increasing costs for producing MDV vaccines. For example, one major United States MDV vaccine producer utilizes 25,000 chick embryos every week. It is estimated that costs associated with purchase and preparation of chick embryos accounts for 40 to 45% of the total cost of MDV vaccine production. A significant reduction in MDV vaccine production costs could be realized if a continuous cell line suitable for vaccine production were established. Requirements for such a cell line are: 1) The cell line can not be virally transformed, 2) Chemically transformed cell lines must be incapable of inducing tumors in vaccinated chickens, and 3) Virus titers produced by such a cell line must be equivalent (or nearly so) to titers obtained through infection of primary cells.

Development of a continuous cell line which would support MDV replication would alleviate many of the difficulties associated with MDV experimentation and vaccine production.

OBJECTS

It is therefore an object of the present invention to provide a sustainable cell line for MDV. Further still, it is an object of the present invention to provide a method for producing the sustainable MDV cell line. Further still, it is an object of the present invention to provide a method for infecting an avian to provide Marek's disease immunity. Further still, it is an object of the present invention to provide methods for producing the MDV cell line which is economical and a method for using the cell line which is effective. These and other objects will become increasingly apparent by reference to the following description and the drawings.

BRIEF DESCRIPTION OF DRAWINGS

FIGS. 1A and 1B are photomicrographs showing uninfected and infected cells. Monolayer of uninfected CHCC-OU2 cells display a cobblestone appearance (FIG. 1A), similar to that seen with primary CEF and DEF. At four weeks post-infection (as set forth in Example 1) numerous plaques consistent with MDV infection were observed on monolayers of Md11p15/OU2 cells (FIG. 1B).

Negative control (lane 1), ICP4 gene promoter sequences (lane 2), 900 bp region of ICP4 coding sequence (lane 3), 1200 bp of BamHI L fragment (lane 4), gC gene promoter sequences (lane 5), US3 gene promoter sequences (lane 6), and UL54 gene sequences (lane 7). Positions of selected bands were obtained from a 1 kb ladder marker, which is not shown (Life Technologies, Inc., Gaithersburg, Md.).

FIG. 3 is an electrophoresis gel showing detection of viral DNA in infected CHCC-OU2 cells. DNA was extracted from cells, digested with BamHI, electrophoresed on 0.8% agarose gels, transferred to Hybond-N-Nylon membranes, hybridized to non-radioactive probe under high stringency conditions, and autoradiographed. Cloned MDV DNA BamHI fragments B, D, F, H, and $I_2$ were used as probes. Locations of each fragment were determined by comparison to a DNA size standard (lambda DNA digested with HindIII) and are indicated by an arrowhead to the left.

FIGS. 4A to 4C are Western blots for detection of specific MDV proteins. Cell lysates from uninfected CEF (CEF), Md11p15 infected CEF (Md11p15), uninfected CHCC-OU2 cells (CHCC-OU2), and Md11p15 infected OU2 cells (MDV OU2.2) were resolved on 12.5% SDS-polyacrylamide gels and transferred to nitrocellulose membranes, followed by immunodetection using specific antisera as described in Materials and Methods. In FIGS. 4A and 4B, positions of molecular size markers (in Kilodaltons), are indicated. FIG. 4A shows detection of MDV-specific protein pp38 using a monoclonal antibody (generously provided by Dr. Lucy Lee, USDA-ADOL, East Lansing, Mich.). FIG. 4B shows detection of MDV-specific protein pp14 using polyclonal antisera generated against pp14 fusion proteins (Hong, Y., and P. M. Coussens, J. Virol. 68:3593–3603 (1994)). FIG. 4C protein loading in each lane was verified by detection of α-actin using a commercial antisera (Santa Cruz Biotechnology, Santa Cruz, Calif.).

FIG. 5 is an electrophoresis gel showing DNA from PCR amplification of 850 bp pp38 gene segment. PCR amplification was carried out on DNA isolated from kidneys of birds injected with CHCC-OU2 (lanes 2 and 3), MDV OU2.2 (lanes 4–6), and Md11p16 infected CEF (lanes 7 and 8). Negative control (lane 1) included all reaction components except template DNA. Additional controls included DNA isolated from uninfected CEF (lane 9), and DNA isolated from Md11p16 infected CEF as positive control (lane 10). In each case (except negative control), 300 ng DNA was used as template for PCR amplification using pp38 specific primers (Table 1). PCR products were analyzed on 12% agarose gels containing 10 μg/ml ethidium bromide. Fragment sizes were determined relative to DNA size standards, which are not shown (1 Kb Ladder, Life Technologies, Gaithersburg Md.).

DESCRIPTION OF PREFERRED EMBODIMENTS

The present invention relates to a sustainable Marek's disease virus (MDV) infected chicken cell line derived from chick embryo cells (CEC) which are chicken helper factor (Chf) negative and virus-free and which have been treated with N-methyl-N$^1$-nitro-N-nitrosoguanidine (MNNG) and then are infected with MDV which is able to infect avians in vivo.

Further, the present invention relates to a method for infecting an avian with Marek's disease virus (MDV) which comprises: providing a vaccine produced by a sustainable Marek's disease virus (MDV) infected chicken cell line derived from chick embryo cells (CEC) which are chicken helper factor (Chf) negative and virus-free and which have been treated with N-methyl-N-nitro-N-nitrosoguanidine (MNNG) and then are infected with MDV which is able to infect avians in vivo; and inoculating the avian with the vaccine.

Finally, the present invention relates to an avian vaccine in dosage unit form containing a sustainable Marek's disease virus (MDV) infected fibroblast cell line derived from chick embryo cells (CEC) which are chicken helper factor (Chf) negative and virus-free and which have been treated with N-methyl-N$^1$-nitro-N-nitrosoguanidine (MNNG) and then are infected with MDV which is able to infect avians in vivo.

The new MDV infected cell lines are "sustainable" which means that it can be maintained in culture for long periods of time (at least nineteen months) without requiring passage. This is a great improvement over multiple passaging in CEC cells as in the prior art.

The virus free cell line CHCC-OU2 is maintained on deposit at Michigan State University and by the USDA and is a known cell line and is freely available upon request. The CHCC-OU2cell line was deposited under the terms of the Budapest Treaty at the American Type Culture Collection (ATCC), 12301 Parklawn Drive, Rockville, Md. 20852, U.S.

A. under the accession number CRL-12302. The CHCC-OU2 cell line will be irrevocably available from the ATCC for the life of the patent. Similarly MDV infected CHCC-OU2 cells deposited under the Budapest Treaty on Sep. 28, 1995, as ATCC CRL-11985 (MDVOU2.2) and is available upon request by name and number. The MDV infected CHCC-OU2 cells will be irrevocably available from the ATCC for the life of the patent.

The MDV infected cell line can be used to produce a vaccine so long as the virus is non-oncogenic. The MDV infected cell line can also be used to test various agents or conditions which suppress or enhance cell response, such as repressing tumor production.

The preferred MDV is a virus selected from Serotypes 1, 2 or 3. Serotype 3 MDV is also referred to as turkey herpesvirus (HVT). The MDV can be a recombinant or deletion mutant which is used as a vaccine or for other uses.

The present invention particularly relates to continuous chick fibroblast cell lines (MDV OU 2.1 and MDV OU2.2), stably infected with MDV strain Md11 at passage level 15. MDV OU2.1 and MDV OU2.2 cells grow continuously in culture and, once confluent, display plaques characteristic of MDV infection. MDV OU2.1 and MDV OU2.2 cells can be used to transfer infection to CEF, and produce classic symptoms of MD in susceptible birds. MDV OU2.2 cells have remained viable and continue to produce MDV after cryogenic storage and continuous culture for over 19 months.

As shown in the following Example 1, Southern blot and PCR analyses demonstrate that these cell lines harbor MDV DNA. Western blot analyses indicate that MDV OU2.2 cells express at least a limited set of viral proteins, pp 38 and pp14, similar to that seen in MDV lymphoblastoid cells. Presence of distinct plaques in confluent MDV OU2.2 cell monolayers is consistent with cytolytic semi-productive infection, similar to that observed in primary CEF. MDV OU2.2 cells are capable of transferring MDV infection to primary CEF cultures and inducing clinical signs of Marek's disease (MD) in susceptible birds. MDV OU2.2 cells have maintained a MDV positive phenotype for over 19 months of active culture.

EXAMPLE 1

MATERIALS AND METHODS

Cells and Virus

Preparation, propagation, and infection of CEF cells with MDV were performed as described previously (Glaubiger, C., et al., J. Virol. 45:1228–1234 (1983); Coussens, P. M., and L. F. Velicer, J. Virol. 62:2373–2379 (1988)). The very virulent MDV strain Md11 was used in this study at cell culture passage level 15 (Md11p15). CHCC-OU2 cells (Ogura, H., et al., Acta Med. Okayama 41:141–143 (1987)) were obtained from Dr. Donald Salter, Avian Disease and Oncology Laboratories (ADOL), U.S. department of Agriculture (USDA), East Lansing, Mich., and were cultured in Leibovitz L15-McCoy 5A (LM) (Gibco, Inc., Grand Island, N.Y.) media (carbon, nitrogen source) supplemented with 10% fetal bovine serum (FBS) and 2% tryptose phosphate broth (TPB) at 37° C. in a humidified atmosphere containing 5% $CO_2$.

CHCC-OU2 cells were infected with MDV strain Md11p15 by combining $5.0 \times 10^7$ CHCC-OU2 cells with $2.0 \times 10^7$ Md11p15 infected CEF prior to plating on 150 mm culture dishes in LM medium supplemented with 4% calf serum (CS). Co-cultivation of CHCC-OU2 cells with Md11 infected CEF cells was continued for four passages. Cells from each of these passages have been preserved at −135° C. in freezing media (LM media (Life Technologies, Gaithersburg, Md., McCoy's 5A medium) supplemented with 20% CS and 10% dimethyl sulfoxide (DMSO). At four passages post-infection, numerous plaques (approximately 100 plaques per 150 mm culture dish), characteristic of MDV infections in CEF cells, were observed. Two of these plaques were isolated using sterile cloning cylinders. Cylinders were placed on top of individual plaques, cells were trypsinized and aspirated from the cloning cylinders. Aspirated cells were transferred to 35 mm culture dishes containing LM media supplemented with 4% CS for expansion. During expansion, cells were not allowed to become confluent and media was changed every 48 to 72 hours. Expanded clones were designated MDV OU2.1 and MDV OU2.2.

Preparation of Cellular DNA, Southern Blot Analysis, And PCR.

Total cellular DNA was extracted from uninfected and MDV-infected CHCC-OU2 cells by standard methods (Sambrook, J., et al., Molecular cloning a laboratory manual, 2nd ed. Cold Spring Harbor Laboratory, Cold Spring Harbor, N.Y. (1989)). Restriction enzymes (Boehringer Mannheim Biochemicals, Indianapolis, Ind.) were used according to the manufacturers recommendation. DNA was digested, electrophoresed through 0.8% agarose gels and transferred to Hybond-N nylon membranes (Amersham Corp., Arlington Heights, Ill.) by Southern blotting (Southern, E. M., Detection of specific sequences among DNA fragments separated by gel electrophoresis. J. Mol. Biol. 98:503 (1975)). Probes were non-radioactively labeled (Digoxigenin-11-dUTP) using a random primer labeling kit (Boehringer Mannheim Biochemicals, Indianapolis, Ind.).

Total cellular DNA was also used as template for PCR amplification of MDV specific sequences. Primers used and expected fragment sizes are indicated in Table 1.

TABLE 1

Sequence of MDV-specific oligonucleotide primers used in PCR amplification.

| Primer Sequences* | Locus | Expected Size (kbp) |
|---|---|---|
| GTAGTGAAATCTATACCTGGG (SEQ. ID. NO. 1) | gC gene promoter | 0.3 |
| GTGTCTAGAGAGGGAAGATATGTAGAGGGTTAC (SEQ. ID. NO. 2) | | |
| ATGGAATTCGAAGCAGAACAC (SEQ. ID. NO. 3) | pp38 gene | 0.85 |
| CTCCAGATTCCACCTCCCCAGA (SEQ. ID. NO. 4) | | |
| TGCTAATTGTGGCTCC (SEQ. ID. NO. 5) | ICP4 gene | 0.9 |
| GGTGCTTCCATCTCGGC (SEQ. ID. NO. 6) | | |
| GATCTAGACGTTTCTGCCTCCGGAGTC (SEQ. ID. NO. 7) | US3 gene | 0.6 |

TABLE 1-continued

Sequence of MDV-specific oligonucleotide primers used in PCR amplification.

| Primer Sequences* | Locus | Expected Size (kbp) |
|---|---|---|
| GCAAGCTTCAACATCTTCAAATAGCCGCAC (SEQ. ID. NO. 8) | promoter | |
| GTCTAGACGCGATAGCGAGTTGTTGGACC (SEQ. ID. NO. 9) | ICP4 gene | 1.1 |
| GGAAGCTTTATTAAGGGAGATTCTACCC (SEQ. ID. NO. 10) | promoter | |
| GTGAAAGAGTGAACGGGAAG (SEQ. ID. NO. 11) | BamHI L | 1.2 |
| CGTCAAAGCGATAATAGGC (SEQ. ID. NO. 12) | fragment | |
| CCGGGGATCCCGAAATGTCGTTAGAACATC (SEQ. ID. NO. 13) | UL54 gene | 1.1 |
| CGGGGTCGACTAAGGCAAATAGGCACGC (SEQ. ID. NO. 14) | | |

*Primer sequences are written as 5' to 3', left to right. In each case, the upper primer represents the upstream sequence while the lower primer represents the downstream sequence. They are set forth in Appendices 1 to 14. Briefly, 300 ng of total cellular DNA was combined with 25 mM each DNTP (DATP, dCTP, dGTP, and dTTP), 20 mM of each appropriate primer pair, 10 μl of 10× PCR reaction buffer (Perkin Elmer Cetus, Norwalk, Conn.), and 2.5 Units Taq polymerase (Perkin Elmer Cetus, Norwalk, Conn.). PCR reactions were performed using a GeneAmp 9600 thermal cycler (Perkin Elmer Cetus, Norwalk, Conn. as follows: 35 cycles of 95° C. for 20 sec, 56° C. for 20 sec. and 72° C. for 30 sec. Two controls, one without DNA and one with uninfected CHCC-OU2 DNA were included in each experiment. High molecular weight DNA isolated from uninfected CEF and CEF infected with Md11p16 were used as controls for specific amplification. PCR products were purified using the Wizard PCR prep kit (Promega Inc., Madison, Wis.) as recommended by the manufacturer) and analyzed on 12% agarose gels.

Western Immunoblot Analysis.

Cultured cells were collected and sonicated using a Sonifier cell disrupter model 350 (Branson Ultrasonic Corporation, Danbury, Conn.). Proteins (20 μg) from each cell type were separated on 12.5% polyacrylamide/1% SDS gels. Separated proteins were electrophoretically transferred to nitrocellulose membranes. Membranes were blocked with 5% nonfat milk and probed with antibodies to MDV proteins: pp14 (Hong, Y., and P. M. Coussens, J. Virol. 68:3593–3603 (1994)), and pp38 (Cui, Z., et al., J. Virol. 65:6509–6515 (1991)). Immune complexes were detected by incubation with a donkey anti-mouse or anti-rabbit immunoglobulin conjugated with horseradish peroxidase. Detection was performed using an ECL Western blot kit (Amersham Corp., Arlington Heights, Ill.) according to the manufacturer's recommendations and exposed to X-ray film. Protein sizes were estimated by comparison to prestained protein molecular weight standards (Bio-Rad, Richmond, Calif.) electrophoresed on the same gel.

Inoculation of Chickens With Cells And Virus.

In vivo experiments were performed using specific pathogen free chickens (line 15I$_5$X 7$_1$) obtained from the Avian Disease and oncology Laboratory, U.S. Department of Agriculture, East Lansing, Mich. Three groups of chicks each at one day of age, were inoculated intraperitoneally with (1) uninfected CHCC-OU2 cells, (2) 1000 plaque forming units (PFU) of Md11p16 in CEF, and (3) 1000 PFU of MDV infected OU2 cells (MDV OU2.2). The first and second groups served as controls (negative and positive, respectively).

Birds were euthanized and necropsied upon signs of morbidity. Blood was collected for isolation of peripheral blood lymphocytes and co-cultivation with CEF as an assay for viable virus. Kidney, spleen, and liver were harvested for DNA isolation and histological evaluation. Total tissue-specific DNA was isolated and used as template for PCR amplification of MDV sequences employing primer sets detailed in Table 1.

RESULTS

Figure 1A:
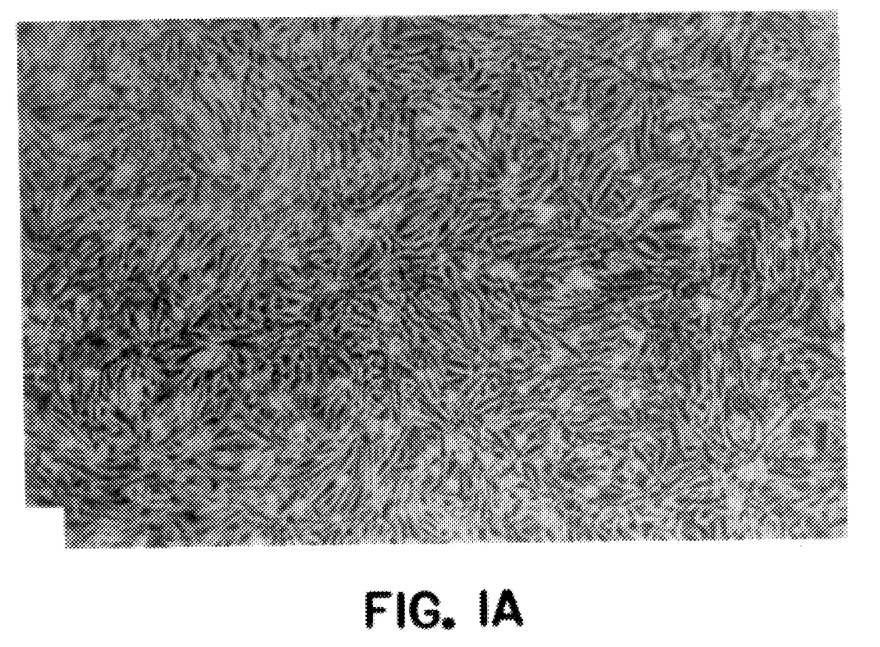
Figure 1B:
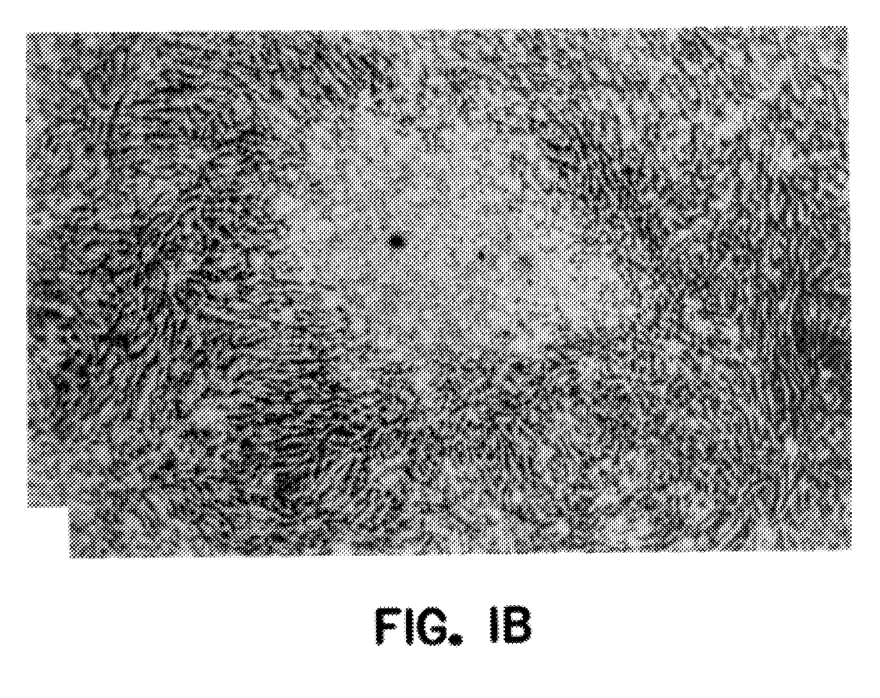

Infection of CHCC-OU2 Cells With Md11p15:

Although CHCC-OU2 cells are chemically immortalized, they are not malignantly transformed, maintain contact inhibition, and exhibit many morphological features of normal chick fibroblasts. CHCC-OU2 cells were co-cultivated with Md11p15 infected CEF cells. Cytopathic effect (CPE), characterized by formation of spherical cells loosely attached to the substratum, was first observed on co-cultivation cell monolayers at two weeks post-infection. The majority of these regions were characterized as "microplaques", consisting of relatively small clusters of rounded cells. CPE was slow in developing and expanding. Fully developed plaques consisting of syncytia and extended regions of rounded, loosely attached, cells were not visible until four weeks post-infection (FIG. 1). The appearance of visible plaques 14 days post-infection and the dependence of plaque formation on the cells reaching confluency and contact inhibition was not expected. By comparison, a typical CEF monolayer infected with MDV strain Md11 will develop readily visible plaques in 5–7 days post-infection with complete destruction of the monolayer within 10–14 days. Plaque formation in CEF is independent of the confluency of the cell monolayer. After four weeks of co-cultivation, cells were cryogenically preserved at –135° C. for two weeks. Cell cultures were re-established from frozen cells by combining infected (Md11p15/OU2) and uninfected CHCC-OU2 cells. Plaques consistent with MDV infection were not observed until cells reached confluency, approximately 14 days post-plating.

Detection of MDV DNA in Infected CHCC-OU2 Cells.

Figure 2:
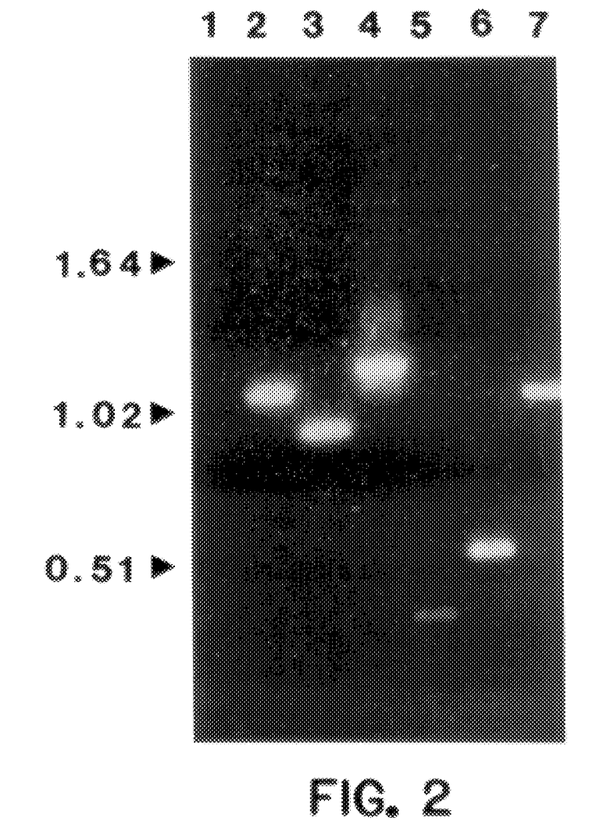
FIG. 2 is an electrophoresis gel showing DNA from PCR amplification Of MDV-specific sequences. PCR amplification was carried out on DNA isolated from Md11 infected CHCC-OU2 cells (lanes 2–6). MDV-specific oligonucleotide primers (Table 1) were used to amplify particular MDV sequences, as set forth in Table 1.

Polymerase chain reaction (PCR) was used as an initial assay for presence of MDV DNA in infected CHCC-OU2 cells. Three hundred ηg of total DNA from Md11p15/OU2 and uninfected CHCC-OU2 cells was used as template for PCR amplification with several primer pairs corresponding to various MDV genes, as described in Materials and Methods. Bands of appropriate sizes (Table 1) were obtained in reactions with Md11p15/OU2 DNA but not from uninfected OU2 DNA templates (FIG. 2). Reactions containing DNA isolated from uninfected CEF and Md11 infected CEF were used as negative and positive controls, respectively (data not shown).

Figure 3:
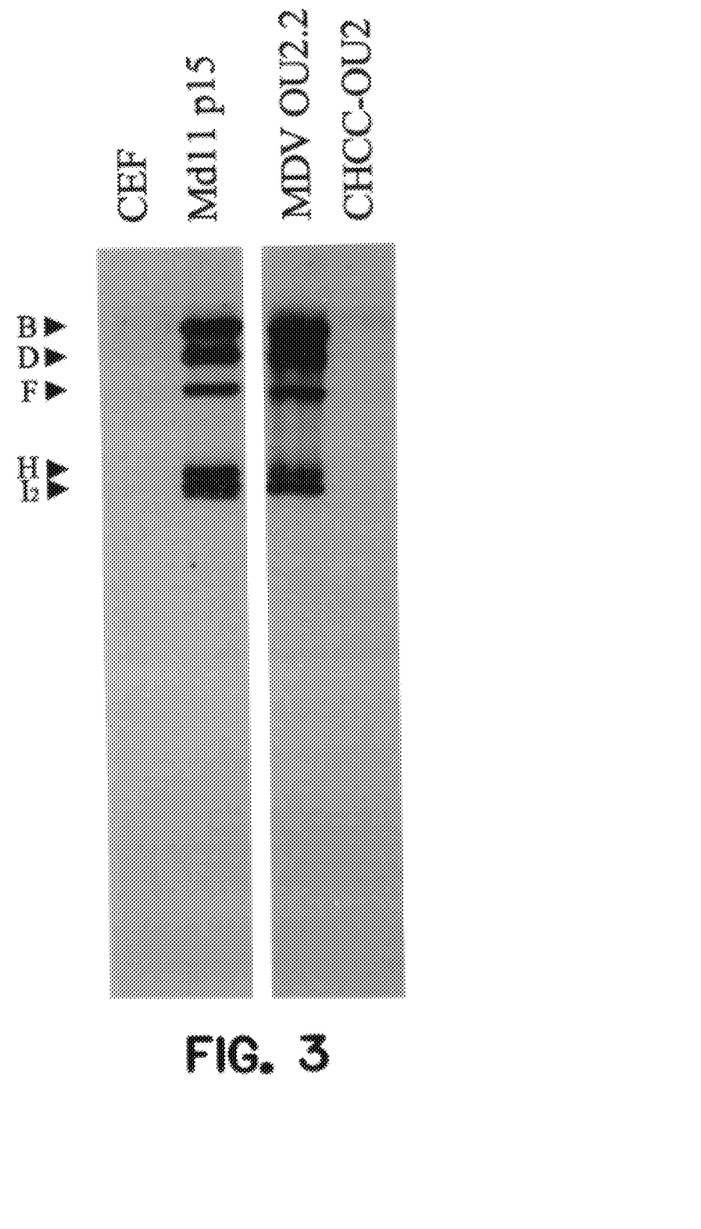

Results of PCR analyses indicated that MDV DNA was present in infected CHCC-OU2 cultures. Although unlikely, given our extended culture conditions, PCR analysis could have detected MDV DNA from residual Md11p15 infected CEF cells. In addition, PCR analyses do not provide critical information on integrity of MDV DNA in Md11p15/OU2 cells. To address these concerns, MDV DNA in infected CHCC-OU2 cells was analyzed by Southern blot hybridization using a cocktail of MDV BamHI fragments (B, F, H, and $I_2$) as a probe. Total genomic DNA isolated from Md11p16 infected CEF and Md11p15/OU2 cells contained MDV specific fragments corresponding to BamHI fragments B, F, H and $I_2$. As expected, similar fragments were not detected in DNA isolated from uninfected CEF or CHCC-OU2 cells (FIG. 3).

Establishment of Infected Cell Lines

Although culture conditions and freeze-thaw cycles should have eliminated most of the original CEF cells used for establishing infection, it was possible that residual CEF cells were contributing to MDV specific DNA detected in our Md11p15/OU2 cultures. To address this concern, isolation and expansion of individual plaques from infected CHCC-OU2 cultures was initiated. Two Md11p15/OU2 cell lines (MDV OU2.1 and MDV OU2.2) were established by plaque isolation and expansion as described in Materials and Methods. Despite arising from distinct plaques, both cell lines exhibited initial growth characteristics indistinguishable from uninfected CHCC-OU2 cells. Plaques characteristic of MDV infection were only observed in MDV OU2.1 and MDV OU2.2 cell cultures after confluency had been reached at 10 to 14 days post-plating.

To confirm infectious virus could be rescued from MDV OU2.1 and MDV OU2.2 cultures, cells from each isolate were used as inoculum to infect CEF cells by combining $1 \times 10^6$ MDV OU2.1 or MDV OU2.2 with $5 \times 10^7$ secondary CEF. Plaque consistent with MDV infection of CEF cells were visible within 5 days post co-cultivation. In contrast, no plaques were evident in control plates containing $1 \times 10^6$ uninfected CHCC-OU2 cells and $5 \times 10^7$ CEF cells.

Detection of Viral Proteins Expressed in MDV OU2.2 cells.

Figure 4A:
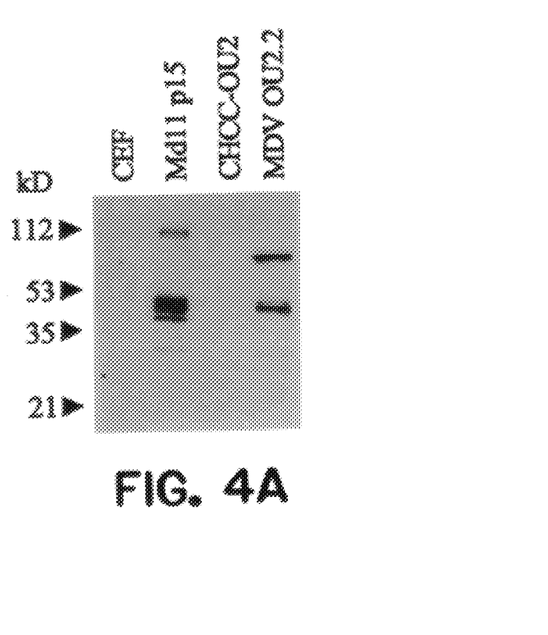
Figure 4B:
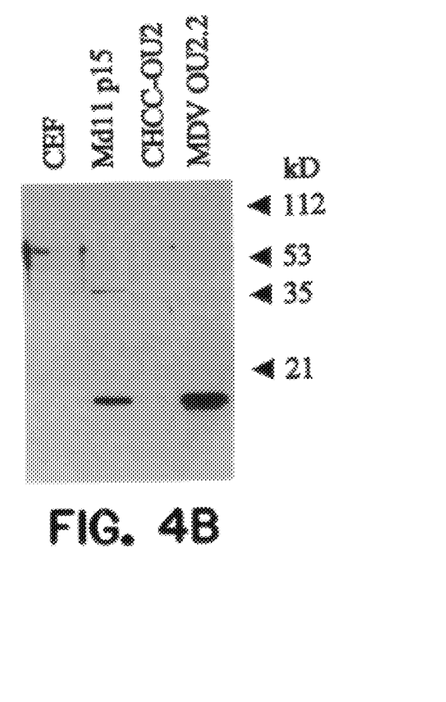
Figure 4C:
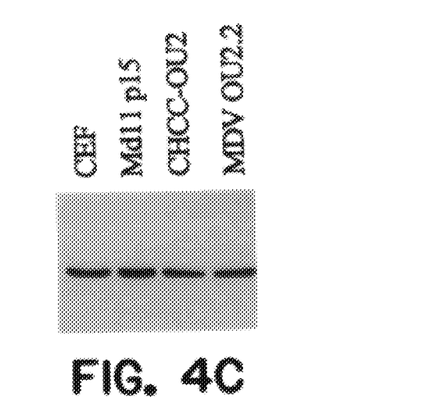
Figure 5:
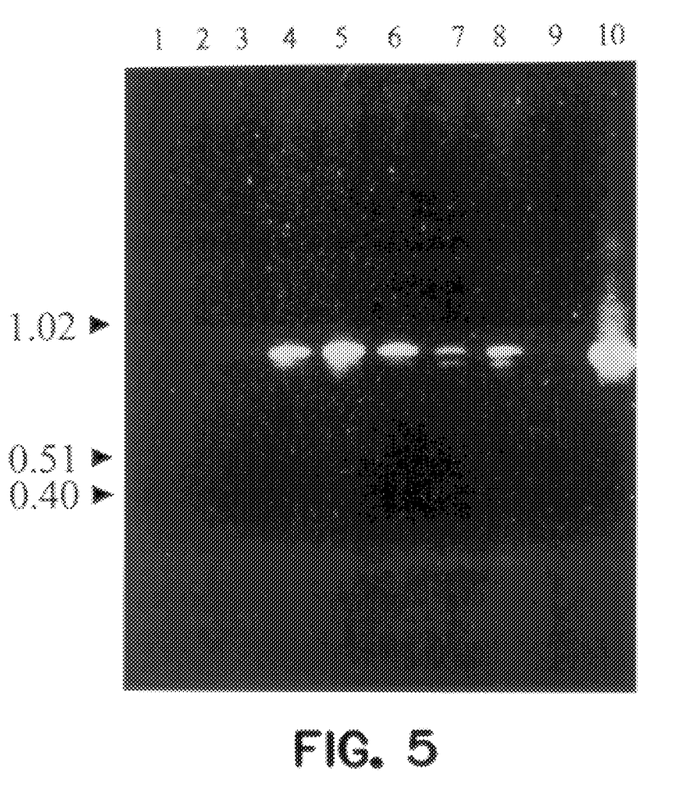

To verify that MDV OU2.2 cells indeed supported replication and growth of MDV, detection of MDV proteins was initiated. Monoclonal antibodies to pp38 (generous gift from Dr. Lucy Lee, USDA-ADOL, East Lansing, Mich.), detected a band of approximately 38 kDa in extracts from confluent MDV OU2.2 cells and Md11p16 infected CEF, but not in extracts from uninfected CHCC-OU2 or CEF cells (FIG. 4A). Polyclonal antisera to pp14, an MDV-specific immediate-early phosphoprotein (Hong, Y., et al., J. Virol. 68:3593–3603 (1994)) also reacted with an appropriately sized polypeptide in extracts from confluent MDV OU2.2 cells and Md11p16 infected CEF cells but not in uninfected cell extracts (FIG. 4B). A polyclonal antisera to a-actin was used to ensure similar amounts of protein were analyzed in each lane (FIG. 4C). Taken together, results of PCR amplification, Southern hybridization, and Western blot analysis indicated that MDV OU2.2 cells represent a continuous anchorage dependent cell line which harbors MDV and is permissive for semi-productive infection.

MDV OU2.2 Cells Induce MD in Susceptible Chickens

Marek's disease can be experimentally induced by injection of MDV infected cells into susceptible birds. MDV lymphoblastoid cell lines such as MSB-1 are also able to induce MD in susceptible birds following intraperitoneal injection. Also, most commercially available MDV vaccines are comprised of CEF cells infected with vaccine strains of MDV. The infectious but apathogenic vaccine strains of MDV are transferred to birds after inoculation where it replicates, inducing humoral and cell mediated responses.

To determine if MDV OU2.2 cells could transfer MDV to birds in a similar manner, line $15I_5X\ 7_1$ chickens were inoculated with uninfected CHCC-OU2 cells, MDV OU2.2 cells, or Md11p16 infected CEF cells at one day of age. Chickens injected with either Md11p16 infected CEF or with MDV OU2.2 cells developed classical signs of MD (reduced growth and paralysis of neck, wings, and legs) as early as 10 days post-infection. In contrast, negative control chickens injected with uninfected CHCC-OU2 cells showed no clinical signs of MD, even at 12 weeks of age.

To confirm presence of MDV in infected birds, peripheral blood lymphocytes (PBLS) were isolated from blood collected at various times post-inoculation and seeded onto secondary CEF. Plaques consistent with MDV infection were observed on CEF monolayers at 4 days post-culture on plates seeded with PBLs isolated from birds injected with Md11p16 infected CEF or MDV OU2.2 cells. No plaques were observed on plates of CEF cells mixed with PBLs obtained from control birds injected with uninfected CHCC-OU2 cells.

To further confirm replication of MDV in infected birds, total cellular DNA isolated from infected bird kidneys was used as template for PCR amplification using primers specific for the MDV pp38 gene. Consistent with the presence of MDV DNA an 850 bp fragment was amplified using DNA isolated from kidneys of birds injected with Md11p16 infected CEF or MDV OU2.2 cells. In contrast, similar bands were not detected when DNA from birds injected with CHCC-OU2 cells was used as template (FIG. 5).

Histological evaluation revealed lymphocyte infiltration and early, active lymphomas in various tissues from birds injected with CEF/Md11p16 and MDV OU2.2, whereas CHCC-OU2 inoculated birds showed no signs of MD at the microscopic level. Taken together, these results clearly demonstrate that MDV OU2.2 cells contain MDV and that the virus may be transferred to birds via intraperitoneal injection.

One of the major difficulties in working with MDV is lack of a sustainable cell culture system for virus growth and selection. Although primary CEF and DEF are permissive for MDV replication, primary cultures are characterized by slow growth and limited life span. These factors necessitate continual passage of infected cells onto uninfected cells in order to obtain sufficient quantities of virus with which to work. In addition, CEF and DEF must be prepared on a regular basis from 10 or 11 day old chick embryos, adding significantly to the expense and difficulty of culturing MDV.

The CHCC-OU2 cell line is an immortalized fibroblastic cell line derived from chick embryo cells (Ogura, H., et al., Acta Med. Okayama 41:141–143 (1987)). CHCC-OU2 are not oncogenic, based on the fact that CHCC-OU2 cells failed to produce tumors when injected into syngeneic chickens (ogura, H., et al., Acta Med. Okayama 41:141–143 (1987)). In addition CHCC-OU2 are virus free and susceptible to avian retrovirus infection (avian sarcoma viruses of subgroups A, B, and C). Newcastle disease virus also replicates well in CHCC-OU2 cell cultures (Ogura, H, et al., Acta Med. Okayama 41:141–143 (1987)).

As can be seen from Example 1, the CHCC-OU2 cells are suitable as a sustainable cell culture system for replication and study of MDV. The initial phase of CHCC-OU2 infection with MDV was slow and characterized by a low number of visible plaques. Fully developed plaques were first observed at four weeks post-infection. At this time, plaques were clearly visible and quite abundant (approximately 100 plaques/150 mm tissue culture plate). In subsequent passages, plaques were visible every 10–14 days in culture.

Southern blot and PCR analyses confirmed that semi-clonal cell lines, MDV OU2.1 and MDV OU2.2, indeed harbor MDV DNA. Fragments detected by Southern blot hybridization were similar in size to those detected in Md11p15 infected CEF, indicating that no gross structural rearrangements had occurred. In addition, fragments detected in MDV OU2.2 cell DNA represent diverse regions of the MDV genome, including the unique long (BamHI B and F), terminal repeat long (BamHI D), and internal repeat long (BamHI H and $I_2$) segments. Intensity of these fragments suggests that MDV OU2.2 cells allow MDV DNA replication, as it is highly unlikely the observed amount of DNA would arise from residual CEF cells used to establish initial infections.

Western blot analyses demonstrated that MDV OU2.2 cells express at least a limited set of viral proteins, pp38 and pp14. Despite numerous attempts, we were unable to detect MDV glycoproteins gC, gB, gE, and gI by western blot analyses. Each of the particular antisera employed was able to detect the respective protein in Md11p15 infected CEF cell extracts. Thus, results of western blot analyses are consistent with MDV existing in MDV OU2.2 cells as a latent infection, similar to that seen in MDV lymphoblastoid cells. However, presence of distinct plaques in MDV OU2.2 cell monolayers is not consistent with latent infection as this would imply cytolytic activity related to MDV infection. However, presence of distinct plaques in confluent MDV OU2.2 cell monolayers imply cytolytic activity related to MDV infection is dependent on contact inhibition.

The in vivo and in vitro experiments demonstrated that in all respects MDV propagated in OU2 cells was structurally and biologically indistinguishable from MDV propagated in CEF. Preliminary experiments with vaccine viruses, SB1 and FC126, indicate that these viruses replicate in the same manner as Md11p15 in OU2 cells. These experiments also indicated that these infected OU2 cells, like OU2 cells infected with Md11p15, are infectious and can transfer virus to CEF. The preliminary data with the vaccine strains of MDV and the in vivo data of Md11p15 suggest that vaccines comprised of OU2 cells infected with vaccine strains of MDV will be just as effective as the current vaccines comprised of CEF infected with vaccine strains of MDV.

EXAMPLE 2

CHCC-OU2 cells were infected with MDV serotype-2 vaccine strain SB1 by infecting CHCC-OU2 monolayers comprised of $4 \times 10^6$ cells on 100 mm culture dishes with $3.1 \times 10^6$ SB1 infected CEF. Co-cultivation was continued for four passages. At every passage, progressively more plaques, characteristic of MDV infections, were observed.

EXAMPLE 3

CHCC-OU2 cells were infected with MDV serotype-3 (HVT) vaccine strain Fc126 by infecting CHCC-OU2 monolayers comprised of $4 \times 10^6$ cells on 100 mm culture dishes with $3.3 \times 10^6$ HVT infected CEF. Co-cultivation was continued for four passages. At passage three, plaques, characteristic of MDV infections, were observed.

In vivo experiments clearly demonstrate that MDV OU2.2 cells are capable of transferring MDV infection to CEF monolayer cultures and inducing clinical signs of MD in susceptible birds. Birds injected with either MDV OU2.2 or Md11p16 infected CEF developed clinical signs of MD, characterized by a marked decrease in growth rate and paralysis of legs, wings, and neck. PCR analysis of tissues, including kidney and spleen, demonstrated that MDV was present in remote tissues of birds injected with MDV OU2.2 cells. In addition, PBLs isolated from birds injected with MDV OU2.2 cells were able to transfer infection to CEF monolayers. In contrast, no evidence of tumor formation or viremia was observed in birds inoculated with uninfected CHCC-OU2 cells.

The in vivo experiments clearly demonstrate that MDV infected CHCC-OU2 cells can be used to establish infections in susceptible birds, a quality of considerable importance for MDV vaccine development and production of MDV mutants by positive selection.

The foregoing description is only illustrative of the present invention and the present invention is limited only by the hereinafter appended claims.

We claim:

1. A sustainable Marek's disease virus (MDV) infected chicken cell line which replicates continuously in cell culture, is contact-inhibited, and produces infectious MDV when the cell culture is confluent, and is able to transfer MDV to avians in vivo which consists of chick embryo cells (CEC) which are chicken helper factor (Chf) negative and virus-free and which have been treated with N-methyl-$N^1$-nitro-N-nitrosoguanidine (MNNG) to render continuously replicating cell line that is not malignantly transformed and is contact-inhibited which is then infected with MDV selected from the group consisting of serotype 1, serotype 2, or serotype 3 MDV, wherein serotype 3 is a turkey herpesvirus (HVT), to establish the sustainable MDV infected chicken cell line.

2. The cell line of claim 1 wherein the MDV is a virus used for the preparation of a virus vaccine to produce immunity.

3. The cell line of claim 1 wherein the MDV is a virus selected from the group consisting of serotype 1, serotype 2, or serotype 3 MDV wherein serotype 3 is a turkey herpesvirus (HVT).

4. The cell line of claim 1 wherein the MDV is a recombinant MDV comprising one or more foreign genes inserted into a site in MDV.

5. The cell line of claim 1 wherein the sustainable MDV infected chicken cell line comprises a recombinant MDV having one or more MDV genes deleted.

6. A sustainable Marek's disease virus cell line deposited as ATCC CRL-11985 containing Marek's disease virus strain Md11.

7. The MDV infected cell line of claim 1 wherein the chick embryo cells treated with MNNG are CHCC-OU2.

8. A method for producing a sustainable Marek's disease virus (MDV) infected chicken cell line which comprises:
 (a) infecting in a culture medium chick embryo cells (CEC) which are chicken helper factor free and virus-free and have been treated with N-methyl-$N^1$-nitro-N-nitrosoguanidine (MNNG) to render a continuously replicating cell line that is not malignantly transformed and is contact-inhibited with an MDV selected from the group consisting of serotype 1, serotype 2, or serotype 3 MDV wherein serotype 3 is a turkey herpesvirus (HVT); and
 (b) purifying the MDV infected continuously replicating cell line; and
 (c) propagating the MDV infected continuously replicating cell line to produce the cell line.

9. The method of claim 8 wherein the MDV is selected from the group consisting of cell-associated MDV derived from primary embryo fibroblasts, cell-free MDV, or MDV DNA transfected into CEC.

10. The method of claim 8 wherein the MDV is a virus used for the preparation of a virus vaccine to produce immunity.

11. The method of claim 8 wherein the MDV is a virus selected from the group consisting of serotype 1, serotype 2, or serotype 3 MDV wherein serotype 3 is a turkey herpesvirus (HVT).

12. The method of claim 8 wherein the MDV is a recombinant MDV comprising one or more foreign genes inserted into a site in MDV.

13. The method of claim 8 wherein the sustainable MDV infected chicken cell line comprises a recombinant MDV having one or more MDV genes deleted.

14. The method of claim 8 wherein the sustainable Marek's disease virus infected chicken cell line is deposited as ATCC CRL-11985 which comprises the Marek's disease strain Md11.

15. The method of claim 8 wherein the cell line derived from chick embryo cells is CHCC-OU2.

16. A sustainable recombinant Marek's disease virus (MDV) infected chicken cell line which consists of chick embryo cells (CEC) which are chicken helper factor (Chf) negative and virus free and which have been treated with N-methyl-$N^1$-nitro-N-nitrosoguanidine (MNNG) to render a continuously replicating cell line that is not malignantly transformed which is then infected with a recombinant MDV to be used for preparation of a virus vaccine to produce immunity, wherein the MDV is selected from the group consisting of serotype 1, serotype 2, or serotype 3 MDV, wherein serotype 3 is a turkey herpesvirus.

17. A method for producing a sustainable recombinant Marek's disease (MDV) infected chicken cell line which replicates continuously in cell culture, is contact-inhibited, produces infectious MDV in confluent cell cultures and is able to transfer MDV to avians in vivo which comprises:

(a) infecting in a culture medium chick embryo cells (CEC) which are chicken helper free and virus-free and have been treated with N-methyl-N$^1$-nitro-N-nitrosoguanidine (MNNG) to render an immortalized cell line that is not malignantly transformed with a recombinant MDV wherein the MDV is selected from the group consisting of serotype 1, serotype 2, or serotype 3 MDV wherein serotype 3 is a turkey herpesvirus;

(b) purifying the recombinant MDV infected continuously replicating cell line; and (c) propagating the recombinant MDV infected continuously replicating cell line to produce the cell line for the preparation of a virus vaccine to produce immunity.

* * * * *